United States Patent [19]

Ingrisano et al.

[11] Patent Number: 4,637,075
[45] Date of Patent: Jan. 20, 1987

[54] EMERGENCY MEDICAL SERVICES SYSTEM

[75] Inventors: Louis A. Ingrisano; Stephen H. Moon, both of Mount Desert; Lawrence J. English, Manset, all of Me.

[73] Assignee: Med-Vest Inc., Mt. Desert, Me.

[21] Appl. No.: 849,013

[22] Filed: Apr. 7, 1986

[51] Int. Cl.[4] .............................................. A41D 1/04
[52] U.S. Cl. .................................................. 2/94; 2/51; 2/102; 2/247; 2/253; 2/DIG. 7
[58] Field of Search ................ 2/94, 51, 93, 102, 108, 2/115, 247, 253, DIG. 7

[56] References Cited

U.S. PATENT DOCUMENTS

| | | | |
|---|---|---|---|
| 2,066,072 | 12/1936 | Powell | 2/51 |
| 3,105,241 | 10/1963 | Allen | 2/94 |
| 3,130,416 | 4/1964 | Mitchell et al. | 2/94 X |
| 3,529,307 | 9/1970 | Belson et al. | 2/94 |
| 3,535,709 | 10/1970 | Johannes | 2/51 |
| 4,041,549 | 8/1977 | Atkinson | 2/94 |
| 4,369,526 | 1/1983 | Clutts | 2/51 |

*Primary Examiner*—H. Hampton Hunter
*Attorney, Agent, or Firm*—Daniel H. Kane, Jr.

[57] ABSTRACT

An emergency medical services (EMS) system for delivering primary care and emergency treatment by EMS personnel is provided by personnel vest jackets constructed and organized for carrying EMS equipment and supplies in wearable and accessible arrangement. The vest is formed with a plurality of outside pockets on the front left and right sides of the vest with first and second large outside pockets across the front bottom left and right sides for carrying bulkier EMS equipment and materials at lower center of gravity. Intermediate size pockets are arranged across the center left and right sides of the vest for carrying intermediate and smaller size EMS supplies. Small upper pockets at least some of elongate configuration are formed on at least one side of the front top of the vest for accommodating objects of elongate configuration. Loop holders are also provided on at least one side of the top front of the vest for holding airways. Quick release loops are provided at the shoulder of the vest for securing the ends a stethoscope around the back of the neck and on the shoulders of the vest. An extra-large pocket is formed across the outside back of the vest for storing and accessing a large multi-trauma dressing pad, abdominal dressing pad or collapsible splint. A full complement of equipment and supplies for emergency medical services is strategically organized on the vest for balance, low center of gravity, accessibility according to frequency of use, etc. The vest construction features facilitate delivery of emergency care.

20 Claims, 8 Drawing Figures

EMERGENCY MEDICAL SERVICES SYSTEM

TECHNICAL FIELD

This invention relates to a new emergency medical services (EMS) system or trauma response system for delivering primary care and emergency treatment. In particular, the invention provides emergency medical technicians, first aid providers and related personnel with trauma servicing vests constructed and organized for carrying EMS equipment and supplies in wearable and accessible arrangement for rapid individual delivery of primary care at the scene of trauma accidents.

BACKGROUND ART

Emergency response to trauma accidents or life threatening medical incidents, and primary care and treatment of bodily injury and illness are generally provided at the scene by emergency medical units, rescue squads and related personnel operating from ambulances and rescue vehicles. EMS equipment and supplies are stored in boxes, containers or bags in the vehicle and are accessed, retrieved and hand carried from the vehicle for delivering primary care or emergency treatment. In response to an emergency call, emergency medical technicians (EMT's) or other first aid providers generally report to a central location and travel to the scene of a trauma incident with the vehicle. Delivery of primary care and emergency treatment is dependent upon the support system provided by the rescue vehicle.

A disadvantage of the prevailing system for emergency medical and trauma response is that the EMT's, paramedics, and first responders must generally operate from or in association with an ambulance or rescue vehicle in order to deliver primary care with EMS equipment and supplies. There is no independent delivery of primary care by multiple responders and the necessity of retrieving materials and equipment from the vehicle in boxes and containers may delay emergency treatment. Because the EMS materials and supplies are stored at the central source, the number of patients and number of locations that can be served at the same time is also limited. An article of clothing in trademarks Class 25 denominated "a vest adapted to receive and carry first aid supplies" is described in the file history of U.S. Trademark Registration No. 1,086,054. However, an unequipped article of vest clothing is illustrated without specification of the essential equipment and supplies necessary for emergency medical and trauma response and primary care. The structure of the vest garment is unsuited for accommodating and supporting the equipment and supplies necessary for emergency medical treatment and independent and individualized delivery of EMS services. There is no discernible design of the vest for ergonomic and accessible arrangement of the essential supplies.

A variety of vest devices are described for other purposes. The LaBove U.S. Pat. No. 4,087,864 describes a dispensing vest worn by patients for receiving intravenous parenteral nutrition. The Paredes U.S. Pat. No. 4,328,533 describes a safety harness or vest which illuminates the user and increases visibility of the wearer at night. The Clutts U.S. Pat. No. 4,369,526 describes a utility vest for workers carrying workers' tools and supplies while the Roberge U.S. Pat. No. 2,992,433 describes a survival jacket or vest with pockets for carrying survival gear.

The Mossfeld Swedish Pat. No. 218,063 illustrates a vest under the title "Medical Training Vest". The configuration of elongate pockets is for accommodating and holding weights for cardiovascular and muscular conditioning and fitness training. None of these vest articles and garments affords the structures for strategic and ergonomic arrangement and accessibility for a full complement of EMS equipment and supplies for responding to trauma accidents and injuries and medical emergencies and none of them includes the package of such materials necessary for independent and individualized delivery of emergency medical services.

OBJECTS OF THE INVENTION

It is therefore an object of the present invention to provide a new emergency medical response and trauma response system which enables EMT's, paramedics or first responders to deliver emergency treatment and primary care from self-contained individualized sources of EMS equipment and supplies. It is intended that the paramedical and first aid personnel be independent from a central source of materials and equipment in the initial phases of primary and first aid care and for most emergency treatments.

Another object of the invention is to provide EMS personnel and trauma responders each with a comprehensive set of EMS supplies and equipment in wearable and accessible arrangement for rapid delivery of emergency treatment to trauma victims on the scene and at remote locations. This ergonomic organization is intended to permit EMS personnel to treat more patients at once at multiple locations and to work independently with the maximum support and least restraint permitted by a portable system.

A further object of the invention is to modify the procedures for delivery of EMS and trauma response services by equipping EMS personnel to respond directly to the scene of a trauma incident without first reporting to a central location for equipment and supplies. The ambulance or rescue vehicle still maintains its own supplies but a self contained package remains with EMS personnel for rapid independent and individualized delivery of primary care.

Finally, the invention intends to provide a wearable package of EMS materials and equipment in an outfit which is ergonomically designed so that a full complement of EMS materials supplies is arranged most conveniently and efficiently according to factors of frequency of use and accessibility, size and weight, and restraint on the wearer. A primary purpose of the invention is thus to provide a cooperating outfit of a wearable vest structure with the essential EMS supplies and materials in synergistic combination for delivery of EMS services by EMS personnel with maximum capability.

DISCLOSURE OF INVENTION

In order to accomplish these results, the present invention provides a new EMS system for delivering primary care and emergency treatment by EMS personnel comprising a personnel vest jacket constructed and organized for carrying EMS equipment and supplies in a wearable and accessible arrangement. The vest is formed with neck, armhole, and waist openings with an overlapping placket extending between the neck and waist openings at the center front with quick release closure such as a Velcro (Trademark) closure or zipper closure for rapidly opening the vest. Quick release loops are provided at the shoulders of the vest for securing the ends of a stethoscope around the back of the neck and on the shoulders of the vest.

The vest is formed with a plurality of outside pockets on the front left and right sides of the vest with the first and second large outside pockets across the front bottom left and right sides respectively of the vest for carrying bulkier EMS equipment and materials at lower center of gravity. Intermediate size pockets are arranged across the center left and right sides of the vest for carrying intermediate and smaller size EMS supplies. Small upper pockets are formed on at least one side of the right and left sides of the front top of the vest with elongate configuration for retaining elongate objects for ready access. Loop holders are also provided on at least one side of the top front of the vest for holding airways.

An extra-large pocket is formed across the outside back of the vest comprising an extra-large pocket cover panel secured at the top and bottom across the back of the vest. The extra-large pocket is openable and accessible on the sides with quick release closures down the sides and tabs for pulling open the sides for storing and accessing a large multi-trauma dressing pad, abdominal dressing pad, or collapsible splints.

At least one of the large outside pockets across the bottom front left and right sides of the vest is a compound pocket having a large inner pocket formed by a first pocket cover panel across the bottom of one side of the vest. An outer pocket is formed by a second pocket cover panel over at least a portion of the first pocket cover panel. The large inner pocket is formed with a quick release closure across at least a portion of the top of the first pocket cover panel. It is contemplated that large gauze bandages and pads and EMT trauma shears be contained in the compound pocket with the EMT trauma shears contained in the outer pocket. The outer pocket may be formed with a side angle contour to accommodate the trauma shears.

In the preferred example embodiment the compound pocket is formed with a quick release closure such as complementary Velcro (Trademark) hook and loop closure material strips along a center width of the top of the first pocket cover panel. The sides of the top of the first pocket cover panel are pleated so that the sides of the large inner pocket are open for quick release of the closure material and access to the large inner pocket.

The other of the large outer pockets is formed with a pocket enclosure panel having a vertical center seam or divider providing two side-by-side pockets to accommodate a blood pressure cuff and a pocket breathing mask. The top of the pocket enclosure panel is gathered with an elastic strip to provide constricted but expandable and accessible openings into the side-by-side pockets.

Alternatively, the other large outer pocket is formed with a pocket enclosure panel having complementary snap enclosure elements spaced apart along the top of the pocket closure panel for pleated constriction of the top of the large outside pocket upon engaging the complementary snap closure elements. A pull tab or loop extends from the top of the pocket enclosure panel for rapid opening of the snap closure elements and access to the pocket. In this embodiment a blood pressure cuff or sphygmomanometer and pocket breathing mask are contained together in the large outside pocket to balance the contents of the compound pocket and maintain a low center of gravity.

In the fully equipped EMS vest according to the invention, smaller gauze bandages and pads, tape, eye pads, note pad and a "space blanket" are contained in the intermediate size pockets across the center of the right and left sides of the vest. A quick release closure flap is formed over the tops of the intermediate size pockets on each side of the vest. A pen and flash light are contained in the small upper pockets of elongate configuration at the top of one side of the vest. Adult and child size airways are secured in the loop holders positioned on the other top front side of the vest.

The EMS vest may also be formed with a plurality of inside pockets including third and fourth large pockets across the bottom inside right and left sides of the vest and a second extra-large pocket across the inside back of the vest. The inside pockets are formed with quick release closures along the top of each inside pocket. It is contemplated that an intravenous (IV) fluid container and and IV administration set may optionally be contained within the third and fourth large pockets across the bottom inside left and right sides of the vest. The center of gravity of the EMS equipped vest is therefore kept low and balanced. Air splints or a cervical collar may be stored in the second extra-large pocket on the inside back of the vest.

The invention also contemplates providing an optional breathing aid in the form of a breathing tube and filter foam block coupled to one end of the breathing tube. The filter foam block is secured to the inside of the vest and arranged with the free end of the breathing tube adjacent to one of the openings of the vest for access for breathing air through the filter foam block in contaminated environments. For example, the filter foam block may be treated for toxic gas filtration as well as particulate smoke elimination. According to another feature of the invention a safety harness is formed around the waist level of the vest, secured at least in part to the inside of the vest for supporting EMS personnel wearing the vest on difficult terrain or working on slopes or inclines while still permitting access to pockets and to the inside of the vest. "D" rings are placed at strategic locations at the ends of the harness and on the vest for further supports.

The invention contemplates a number of other construction features. The neck, arm hole, and waist openings of the vest comprise flexible material borders for nonbinding close fit of the vest on EMS personnel wearing the vest. The vest jacket may be constructed from fire retardent material or material such as Gortex (Trademark) that repels water but breathes air. Alternatively, ventilation strips may be included in the construction. Reflector strips are placed strategically over the vest for example along the placket and intermediate size pocket vest flaps forming a "T" on the front of the vest, and along the top of the extra-large pocket on the back of the vest. A name plate may optionally be placed above the extra-large pocket across the back of the vest. For the quick release closures, complementary hook and loop material strips such as Velcro (Trademark) strips or zipper closures are used.

A feature and advantage of the invention is that EMS personnel and first responders including EMT's, medics, paramedics, nurses, first responders and first aid providers carry with them individually and independently all the EMS equipment and supplies essential for the initial phases of primary and emergency care and for 90% of emergency treatments. The self contained individualized support system is packaged in the form of a personnel vest for ergonomic accessibility of all EMS supplies with minimum restraint and maximum mobility and capability. The delivery of EMS services and response to trauma accidents is dramatically changed so that EMS personnel respond directly to the scene of an accident or medical incident fully equipped to offer primary care.

Other objects, features, and advantages of the invention are set forth in the following specification and accompanying drawings.

DETAILED DESCRIPTION OF PREFERRED EXAMPLE EMBODIMENTS AND BEST MODE OF THE INVENTION

Figure 1:
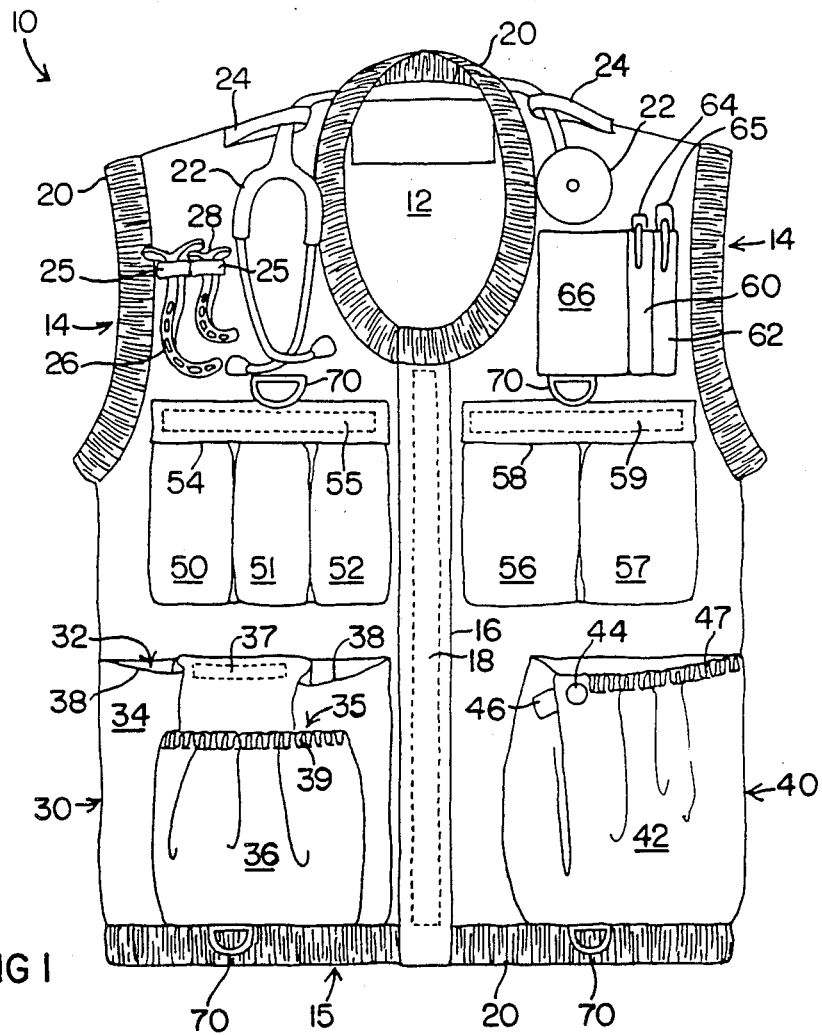
FIG. 1 is a diagrammatic plan view of the front of an EMS vest according to the present invention showing the strategic arrangement of EMS equipment and supplies.
Figure 1A:
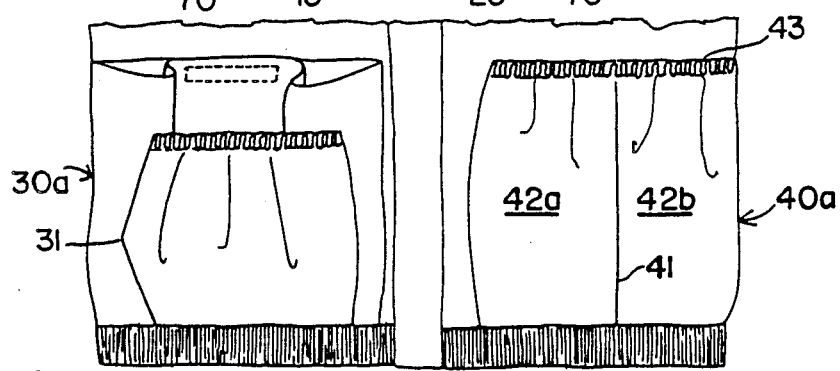
FIG. 1A is a fragmentary plan view of the lower front of the EMS vest showing a preferred construction for the large outer pockets.
Figure 1B:
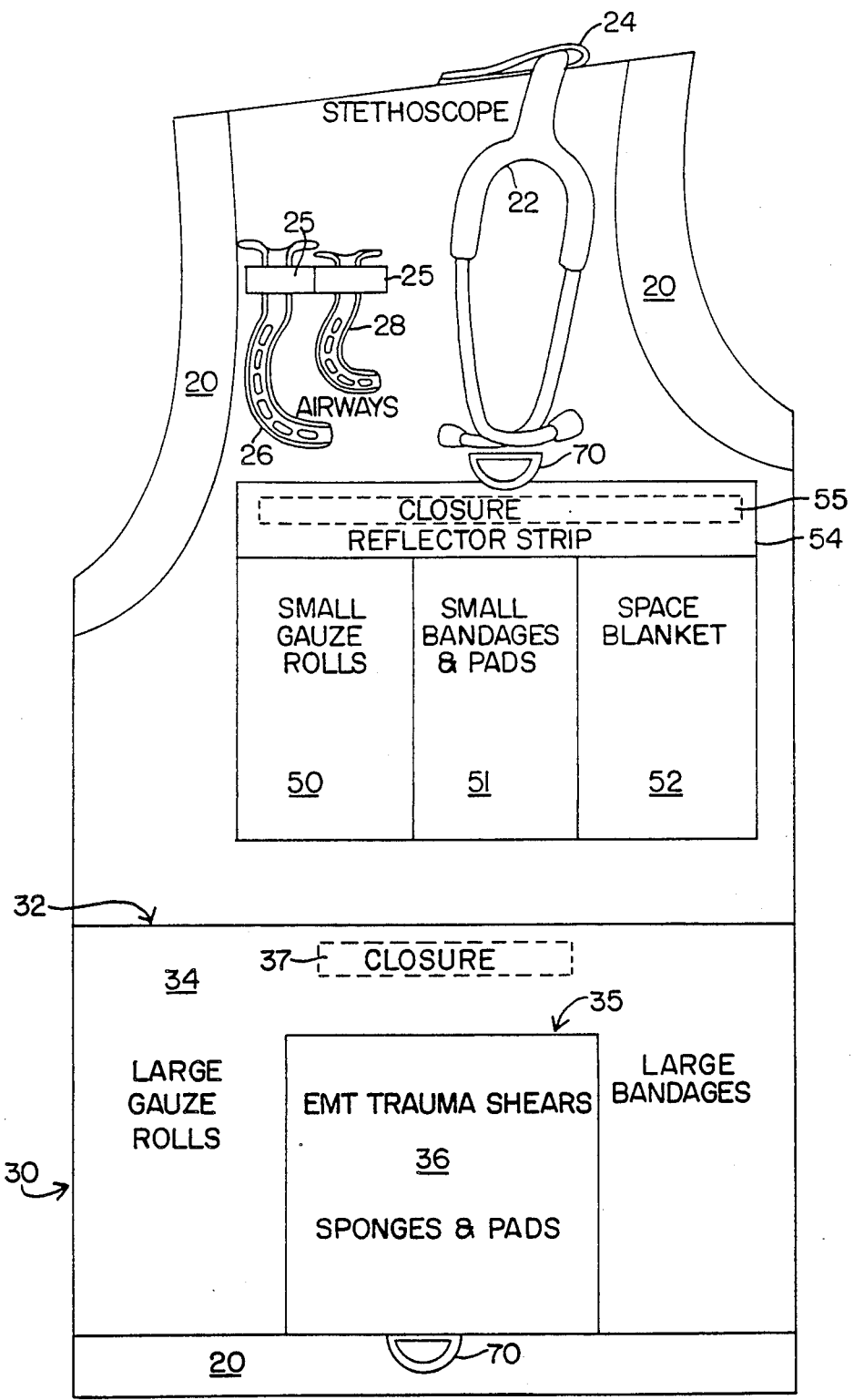
FIGS. 1B and 1C are diagrammatic plans showing the layout and organization of EMS equipment on the front right and left sides of the EMS vest.
Figure 2:
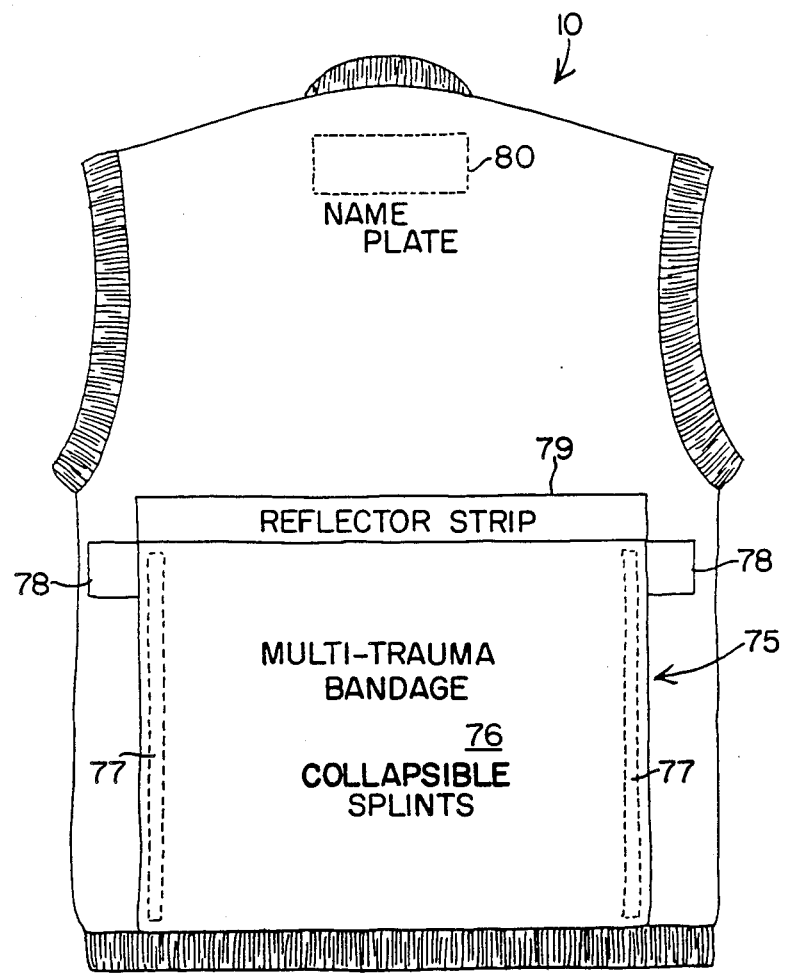
FIG. 2 is a diagrammatic plan view of the back of the EMS vest.

An emergency medical response vest according to the invention is illustrated in FIGS. 1 and 2 with detailed diagrammatic views of the front right and left sides of the vest in FIGS. 1A and 1B showing the layout of the vest structure and arrangement of EMS equipment and supplies carried on the vest. The personnel vest or vest jacket 10 is formed with a neck opening 12, armholes 14, and waist opening 15 with an over-lapping placket 16 extending between the neck opening 12 and waist opening 15 at the center front of the vest. Quick release closure strips 18 line the side edges of the vest below the placket 16 for rapidly opening and closing the vest. Alternatively a zipper closure is used. The outside front of the placket 16 is covered over its entire length with a reflective tape strip. The respective neck, arm and waist openings 12, 14 and 15 are formed with flexible material borders 20 such as jersey-knit borders or hems for non-binding close fit of the vest 10 on EMS personnel.

A vital instrument of emergency medical response is the stethoscope 22 which is carried around the neck opening 12 and over the shoulders of the vest by a pair of stethoscope retaining loops 24 placed on the shoulder seams on either shoulder. The retaining loops 24 are quick release loops formed for example of Velcro (Trademark) strips or ends for quickly opening the loops to retrieve the stethoscope 22. These quick release stethoscope retaining loops 24 are spaced from the neck opening 12 and neck border or hem 20 so that the length of the stethoscope 22 lying on its side is distributed along and over the shoulders.

A pair of elastic loops 25 are placed at the top right front side or right front shoulder of the vest for holding an adult-size airway 26 and child-size airway 28 for establishing an airway. The loops 25 may also be oriented along a diagonal line extending between the center of the neck opening 12 and the bottom of the armhole 14 at approximately a 45 degree angle relative to the horizontal so that the airways lie diagonally across the area between the armhole and neck. Because the airways are less frequently used, they are for that reason positioned at the upper right quadrant or quarter of the vest where they are accessed and recovered with the left hand. More frequently used items are located at the upper left corner of the vest where they are easily accessed by the right hand.

The vest is formed with three levels of pockets on the front of the vest and simultaneous reference is made to FIGS. 1 and 1B. The large front pockets are formed across the front bottom right and left sides of the vest for carrying bulkier or heavier EMS equipment and materials at lower center of gravity. One of the large outside pockets across the bottom front right and left sides of the vest, pocket 30, in this example located at the bottom front right of the vest, is a compound pocket. Compound pocket 30 includes a large inner pocket 32 formed by a first pocket cover panel 34 across the bottom right side of the vest, and an outer pocket 35 formed by a second smaller pocket cover panel 36 secured over at least a portion of the first pocket cover panel 34.

The large inner pocket 32 of compound pocket 30 is formed with a quick release closure 37 along a center width only of the top edge of the first pocket cover panel 34. The closure strip along the center of inner pocket 32 is provided, for example, by complementary Velcro (Trademark) or other hook and loop closure material strips. The sides 38 of the inner pocket cover panel or gore 34 on either side of the center closure 37 are open and may be pleated to contain the top of the pocket while permiting rapid access to the large inner pocket 32. The top edge of the second pocket cover panel 36 of the outer pocket 35 is sewn with an elastic strip 39 along the inside edge to contain the pocket while permitting the rapid access.

The other large pocket 40 located at the lower left side of the vest may be formed as shown in FIG. 1 with a pocket enclosure panel 42 having complementary snap closure element 44 spaced apart approximately a third of the length along the top of the pocket enclosure panel 42 for closing and containing the top of the large pocket 40. A pull tab 46 extends from the top edge for quick opening of the snap closure elements and access to the pocket. The remaining two-thirds length of the top edge of pocket cover panel 42 may be formed with an elastic strip 47 for access to the pocket 40 even with the snap elements closed. According to this arrangement a pocket breathing mask for mouth to mouth resuscitation and a blood pressure cuff or a sphygmomanometer are both contained in the large pocket 40 on the bottom left hand side.

Figure 1C:
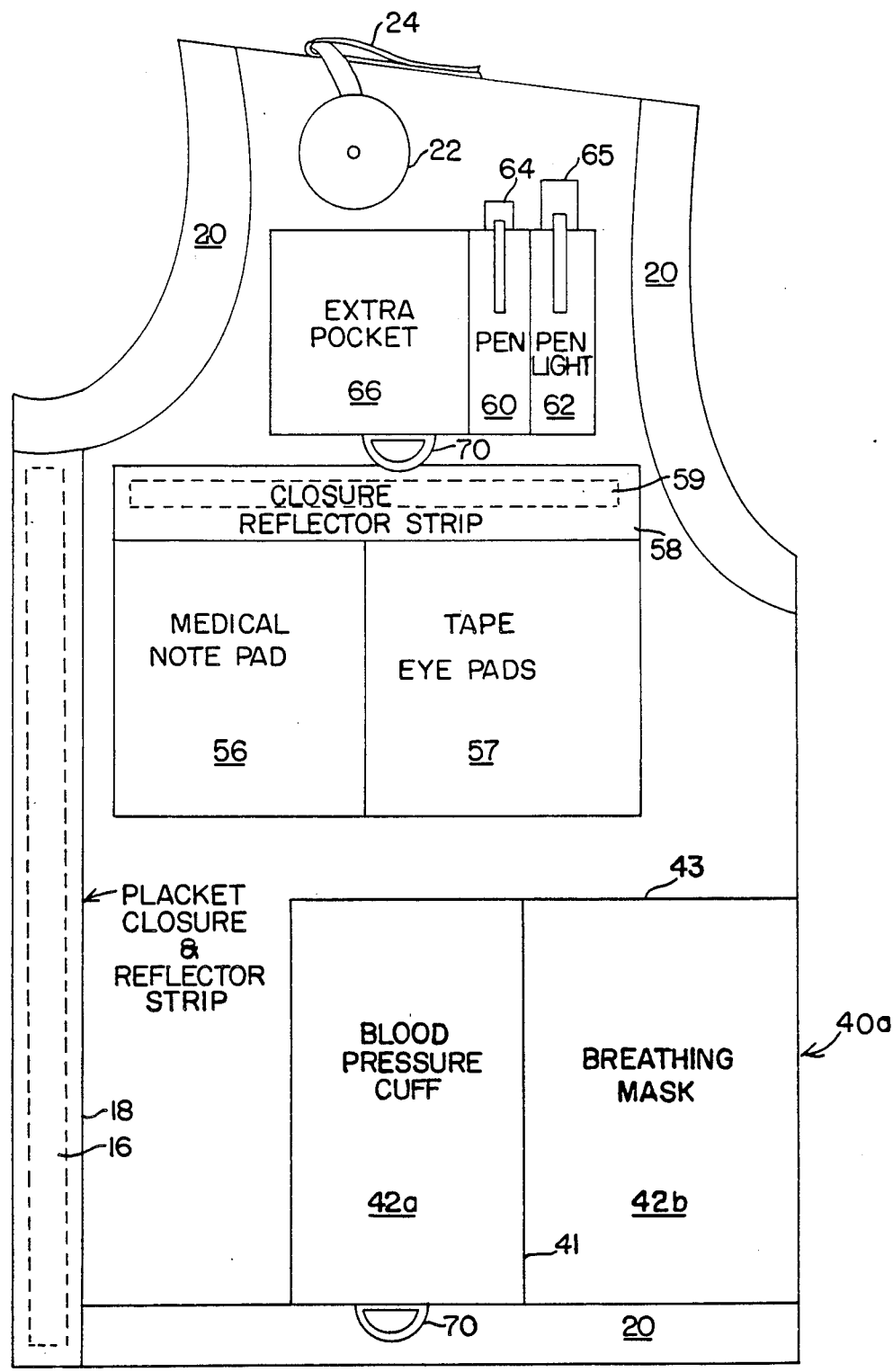

In the preferred embodiment as shown in FIGS. 1A and 1C, the large outer pocket 40a is formed with a pocket enclosure panel having a vertical center seam or divider 41 providing two side-by-side pockets 42a and 42b. The top edge 43 of the dual or double pocket 40a is gathered and sewn with an elastic strip to provide retained but expandable and accessible openings into the side-by-side pockets 42a and 42b. A blood pressure cuff is contained in the double pocket side 42a while a breathing mask is held in the dual pocket side 42b.

On the bottom right hand side large gauze rolls and bandages such as the six inch (15 cm) gauze rolls or bandages are held in the large inner pocket 32 of compound pocket 30 while EMT trauma sheers or scissors and sponges and pads may be contained in the outer pocket 35 of the compound pocket 30. By this arrangement the bulkier EMS equipment and supplies are carried with a lower center of gravity and balanced on either side of the center of the vest. In a preferred embodiment illustrated in FIG. 1A, the outer pocket cover panel 36a of outer pocket 35a is contoured with an obtuse angle 31 along the right side to accommodate the bent or angled blades characteristic of EMT trauma shears.

Intermediate sized pockets are formed across the center right and left sides of the vest. The three intermediate size pockets 50, 51 and 52 across the center right side of the vest are formed with a single unitary flap 54 covering the tops of all three pockets. The flap 54 is formed with a quick release closure in the form of complementary hook and loop material strips 55 such as Velco (Trademark) strips. The pair of intermediate size pockets 56 and 57 on the center left side of the vest are similarly formed with a single unitary flap 58 which closes over the tops of the intermediate size pockets 56 and 57 with quick release closure strips 59.

The unitary flaps 54 and 58 are each formed with reflector strip material along the length of the outside of the flap. As a result the flaps 54 and 58 form a reflecting "T" configuration with the plaquet 16 across the front of the vest 10.

According to the preferred arangement intermediate size pockets 50 and 51 contain the small gauze rolls and bandages for example three inch (7.6 cm) gauze rolls and bandages while intermediate size pocket 52 contains a space blanket, an emergency body heat reflecting thermal blanket of space blanket material. The intermediate size pocket 56 may carry a medical note pad for taking medical notes or alternatively additional bandages while intermediate size pocket 57 carries adhesive tape and eye patches or eye pads.

A third level of pockets or shoulder pockets are formed at the upper left front of the vest including a pair of small pockets 60 and 62 of elongate configuration for accommodating elongate objects, and in the preferred example arrangment a pen 64 and pen light 64. The location at the upper left quadrant or upper left corner of the vest makes the pen 64 and pen light 65 readily accessible to the right hand. An extra pocket 66 of small to intermediate size is also provided at the front of the upper left corner of the vest and may be used for example to hold a medical note pad if small bandages are contained in the intermediate size pocket 56 below. Alternatively the extra pocket 66 is used to hold an IV administration set.

It is apparent that a combination of principles inhere in the arrangement of the structure of the vest and the EMS equipment and supplies carried on the vest. To the extent permitted the EMS supplies and equipment are distributed substantially evenly by weight and bulk over the front of the vest for balance, and distributed with larger and bulkier items in the lower quadrants of the vest for lower center of gravity. Furthermore, the pieces of equipment and material are arranged with an eye towards frequency of use and therefore relative ease of accessibility from the stethoscope secured around the neck and along and over the shoulders of the vest by quick release loop forming strips to the blood pressure cuff or sphygmomanometer in one of the large lower pockets. "D" rings 70 are also strategically located at the center of the four quadrants or corners of the vest for lashing and supporting additional equipment where necessary or for accommodating support lines or belts.

The back of the personnel vest 10 of FIGS. 1, 1A and 1B is illustrated in FIG. 2. Across the outside of the lower back of the vest an extra-large pocket is formed by an extra-large pocket cover panel 76 secured along the top and bottom of the panel across the back of the vest. The extra-large pocket 75 is openable and accessible on the sides through quick release closure 77 formed by complementary closure material strips down the sides of the extra-large cover panel 76. Pull tabs or loops 78 facilitate opening the sides of the extra-large pocket 75 while a reflector strip 79 is positioned along the top seam of the pocket.

According to the preferred example arrangement at least one large multi-trauma bandage, abdominal bandage, or collapsible splints are stored in the extra-large pocket 75 with ready access through the sides of the pocket. A name plate 80 may optionally be included at the top of the back to identify the EMT or other personnel wearing the vest.

Figure 3:
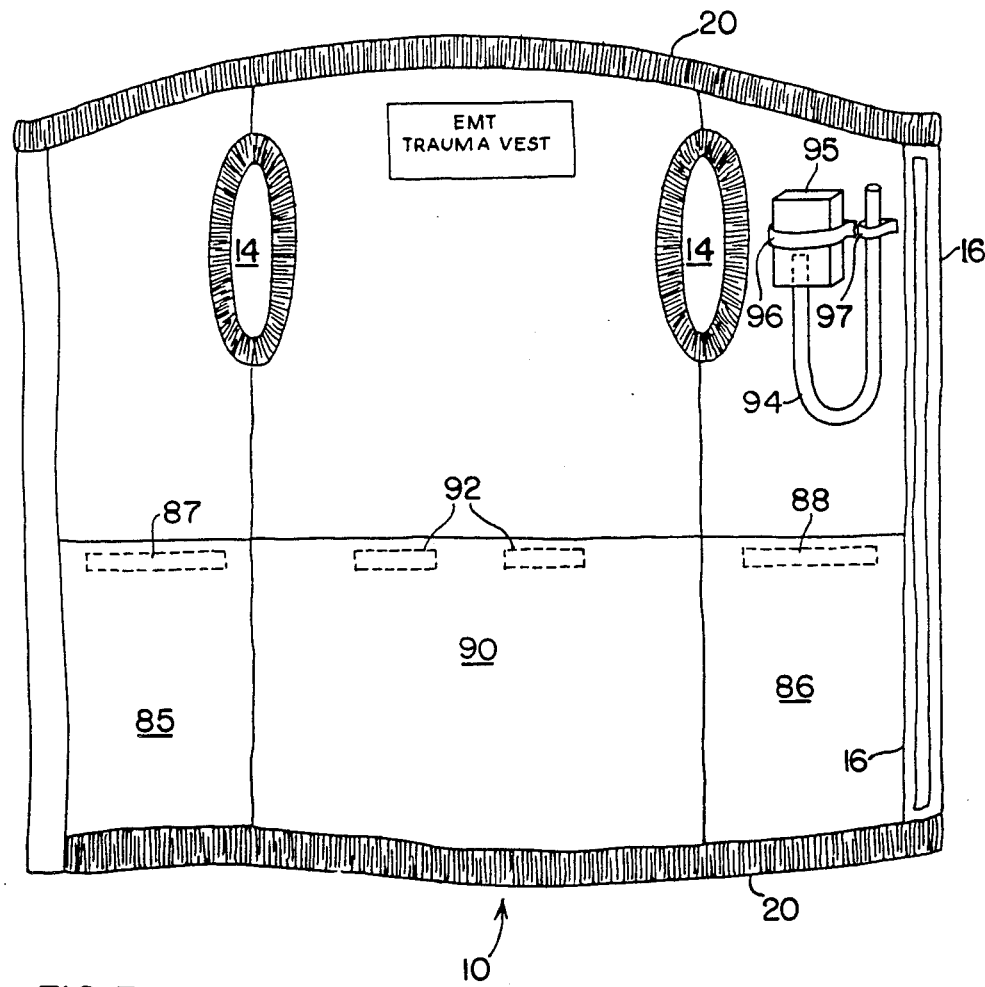
FIG. 3 is a diagrammatic plan view of the inside of the EMS vest with the placket opened and showing the layout of the inside of the vest.

A diagrammatic representation of the inside of the vest is illustrated in FIG. 3 showing the arrangement of available inside pockets. Additional large pockets 85 and 86 are provided across the bottom of the inside right and left sides of the vest with quick release closures 87 and 88 in the form of complementary strips formed along a center portion of the top of each pocket for rapid access. A second extra-large pocket 90 is formed across the inside back of the vest similarly accessible from the top through quick release closure 92. According to one alternative embodiment and arrangement of the invention, an intravenous or IV fluid container and IV administration set may be carried in the right and left large inside pockets 85 and 86 respectively for balance and low center of gravity while an additional multi-trauma bandage or abdominal (ABD) bandage may be stored in the inside extra-large pocket 90. The air splints may optionally be stored in the inside extra-large pocket 90 also or alternatively, a cervical collar may be stored at this location.

According to the invention a breathing aid may also be stored on the inside of the vest for example at the top left or right inside of the vest in the form of a breathing tube 94 and filter foam block 95 coupled to one end of the breathing tube. The filter foam block is secured to the inside of the vest by a strap 96 while the free end of breathing tube 94 is removably held by the quick release loop 97. The free end of the breathing tube 94 is arranged so that it is quickly accessible for example through the placket 16 of the vest 10 or through one of the openings in the vest for breathing air through the filter foam block 95 in contaminated environments. The filter foam block 95 may be, for example a composite active filter material and open cell or reticulated foam substrate of the type described in U.S. patent application Ser. No. 689,249, filed Jan. 7, 1985, for "Composite Active Filter Material". The composite filter material filters the contaminated air for removal of toxic gases as well as smoke particles. The end of the breathing tube 94 is seated in the filter foam block 95 so that breathing air drawn through the free end of the tube is constrained to pass through the filter foam block.

Figure 4:
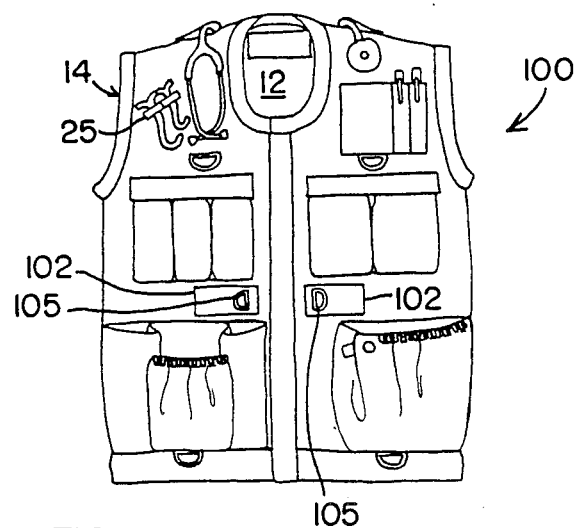
FIG. 4 is a diagrammatic plan view of a simplified vest showing placement of a safety harness or belt according to the invention and an alternative arrangement of the airway retaining loops.
Figure 5:
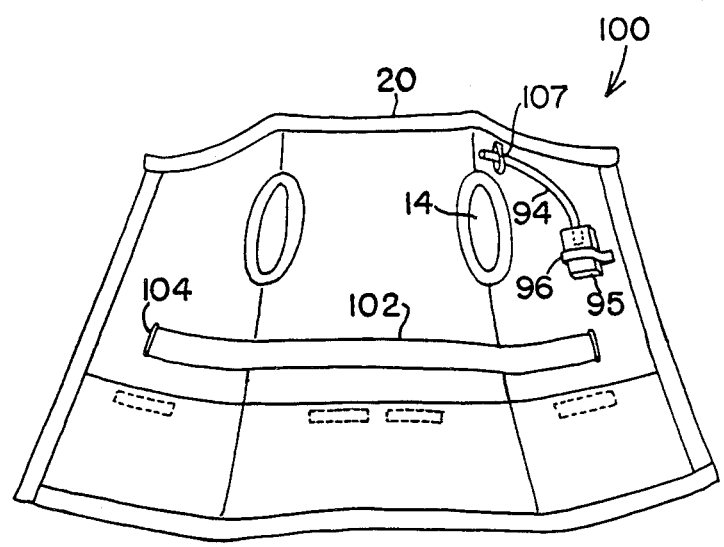
FIG. 5 is a diagrammatic plan view of the inside of the simplified vest showing placement of a safety harness or belt and an alternative orientation for the breathing aid.

A further embodiment contemplated by the invention is illustrated in FIGS. 4 and 5 showing an EMS personnel vest of the type illustrated in FIGS. 1 and 2 with the addition of the safety harness. The safety harness EMS vest 100 illustrated in FIGS. 4 and 5 includes the structural elements and EMS equipment and supplies described with reference to FIGS. 1 and 2 and in addition a safety belt or harness 102. The safety harness 102 is formed around the waist of the vest with a major center length of the belt or harness 102 located and secured on the inside of the vest as shown in FIG. 5. The harness passes through openings 104 at the front of the vest passing to the outside of the vest for coupling or securing for example to safety lines through the "D" rings 105 at the ends of the harness. By this arrangment, the harness or belt 102 may be used for supporting EMS personnel wearing the vest on difficult terrain, on slopes and on inclines while still permitting access to pockets on the vest and to the inside of the vest.

A preferred orientation of the airway retaining loops 25 is shown in FIG. 4. In this arrangement the loops 25 are aligned along a diagonal line between the side of neck opening 12 and bottom of armhole 14 so that the airways lie diagonally across the space between the neckhole and armhole.

An alternative support arrangement for the breathing aid is also illustrated in FIG. 5. In this example the filter foam block 95 is similarly supported by a strap 96 as described above. The breathing tube 94 however is supported by a quick release retaining loop 107 positioned between the arm hole 14 and neck opening bordered by hem 20 so that the free end of the breathing tube may be accessible either through the neck opening or through the arm hole.

While the invention has been described with reference to particular example embodiments it is intended to cover all modifications and equivalence within the scope of the following claims.

We claim:

1. An emergency medical system (EMS) system for delivering primary care emergency treatment and EMS equipment and supplies by EMS personnel comprising:
   a personnel vest constructed and organized for carrying EMS equipment and supplies in a wearable and accessible arrangement, said vest being formed with a neck, two armholes and a waist opening, and an overlapping placket at the center front of the vest extending between the neck and waist openings, said placket being formed with closure means;
   quick release support loops at the shoulders of the vest for securing the ends of a stethoscope and for carrying a stethoscope around the back of the neck and on the shoulders of EMS personnel wearing the vest;
   said vest comprising a plurality of outside pockets arranged on the front left and right sides of the vest with first and second large outside pockets across the front bottom left and right sides respectively of the vest for carrying bulkier EMS equipment and supplies at lower center of gravity and a plurality of intermediate size pockets across the center left and right sides of the front of the vest for carrying intermediate and smaller size EMS equipment and supplies;
   at least one of said large outside pockets across the bottom front left and right sides of the vest comprising a compound pocket having a large inner pocket formed by a first pocket cover panel across the bottom of one side of the vest and an outer pocket formed by a second pocket cover panel over at least a portion of the first pocket cover panel, said large inner pocket being formed with quick release closure means across at least a portion of the top of the first pocket cover panel;
   said intermediate size pockets across the center of the right and left sides of the vest being formed with quick release closure flap means over the tops of the intermediate size pockets;
   small upper pockets formed on at least one side of the right and left sides of the front top of the vest at least one of said upper pockets having narrow elongate configuration for retaining elongate objects for ready access;
   loop holding means formed on at least one side of the top front of the vest for holding airway means;
   and a first extra-large pocket formed across the outside back of the vest comprising an extra-large pocket cover panel secured along the top and bottom across the back of the vest, said extra-large pocket being openable and accessible on the sides and formed with quick release closure means along the sides and with tabs for pulling open the sides for storing and accessing a large multi-trauma dressing pad.

2. The EMS system of claim 1 wherein the compound pocket is formed with quick release closure means along a center width of the top of the first pocket cover panel so that the sides of the large inner pocket are open for quick release of the closure means and access to the large inner pocket.

3. The EMS system of claim 1 wherein one of said large outside pockets across the bottom left and right sides of the vest is formed with a pocket enclosure panel having a vertical center seam or divider forming dual side-by-side pocket elements, the top edge of the pocket enclosure panel being formed with an elastic strip for constricting the top of said pocket elements while permitting expansion and access into said pocket elements.

4. The EMS system of claim 3 further comprising a blood pressure cuff or sphygmomanometer and pocket breathing mask contained in respective dual pocket elements of said one of the first and second large outside pockets, and large gauze bandages and pads and EMT trauma shears contained in the compound pocket comprising the other large outside pocket thereby balancing the bottom left and right sides of the vest.

5. The EMS system of claim 4 wherein the large gauze bandages and pads and EMT trauma shears are contained in the compound pocket with the shears in the outer pocket of the compound pocket and wherein the outer pocket of the compound pocket is contoured with an obtuse angle on one side to accommodate the EMT trauma shears.

6. The EMS system of claim 4 further comprising relatively smaller gauze bandages and pads, tape, eye pads and note pad contained in the intermediate size pockets across the center of the right and left sides of the vest.

7. The EMS system of claim 6 further comprising a stethoscope retained in the quick release support loops at the shoulders of the vest so that the stethoscope lies around the back of the neck and along the shoulders and comprising adult and child airways retained in the loop holding means on one side of the top front of the vest.

8. The EMS system of claim 7 comprising a multi-trauma dressing pad contained within the outside back pocket of the vest.

9. The EMS system of claim 8 further comprising collapsible splints contained within the outside back pocket of the vest.

10. The EMS system of claim 8 further comprising pen means and flash light means contained within the small upper pockets of narrow elongate configuration at the top front of one side of the vest.

11. The EMS system of claim 1 further comprising a plurality of inside pockets including third and fourth large pockets across the bottom inside right and left sides of the vest and a second extra-large pocket across the inside back of the vest, said inside pockets being formed with quick release closure means along the top of each inside pocket.

12. The EMS system of claim 11 further comprising an intravenous fluid container and an intravenous administration set contained within the third and fourth large pockets across the bottom inside right and left sides of the vest.

13. The EMS system of claim 1 comprising a breathing tube and filter foam block coupled to one end of the breathing tube, said breathing tube and filter foam block being secured to the inside of the vest and arranged with the free end of the breathing tube adjacent to an opening of the vest for access for breathing air through the filter foam block.

14. The EMS system of claim 1 wherein the neck, two arm holes and waist opening of the vest comprise flexible material borders formed around said neck, arm holes and waist opening for nonbinding close fit of the vest on EMT personnel wearing the vest.

15. The EMS system of claim 1 further comprising a safety harness formed around the waist of the vest, said safety harness comprising a belt secured at least in part to the inside of the vest around the waist to permit access to the pockets and to permit the vest to be open while supporting EMS personnel wearing the vest.

16. An emergency medical services (EMS) system for delivering primary and emergency care with EMS equipment and supplies by EMS personnel comprising:
a personnel vest constructed and organized for carrying EMS equipment and supplies in a wearable and accessible arrangement, said vest being formed with a neck, arm holes, waist openings, and an overlapping placket at the center front of the vest extending between the neck and waist opening, said placket being formed with closure means for rapidly opening the vest;
said vest comprising quick release support loops at the shoulders of the vest for securing the ends of a stethoscope, and a stethoscope carried around the back of the neck and on the shoulders of the vest;
said vest comprising a plurality of outside pockets arranged on the front left and right sides of the vest with first and second large outside pockets across the front bottom left and right sides respectively of the vest for carrying bulkier EMS equipment and supplies at lower center of gravity and a plurality of intermediate size pockets across the center left and right sides of the front of the vest for carrying intermediate and smaller size EMS equipment and supplies;
at least one of said outside large pockets across the bottom front left and right sides of the vest comprising a compound pocket having a large inner pocket formed by a first pocket cover panel across the bottom of one side of the vest and an outer pocket formed by a second pocket cover panel over at least a portion the first pocket cover panel, said large inner pocket being formed with a quick release closure means across a center width of the top of the first pocket cover panel, the sides of the top of the first pocket cover panel being open for quick release of the closure means and access to the large inner pocket, and large gauze bandages and pads and EMT trauma sheers contained in the compound pocket with the EMT trauma sheers contained in the outer pocket of the compound pocket;
the other of the large outside pockets across the front bottom left and right sides of the vest being formed with a pocket enclosure panel having a vertical center seam or divider forming dual side-by-side pocket elements, the top enclosure panel being formed with an elastic strip for constriction of the top of said pocket elements while permitting expansion and access into said pocket elements, and a blood pressure cuff or sphygomomanometer and pocket breathing mask contained respectively in said dual pocket elements;
said intermediate size pockets across the center of the right and left sides of the vest being formed with quick release closure flap means over the tops of the intermediate size pockets and relatively smaller gauze bandages and pads, tape, eye patch and note pad contained in the intermediate size pockets across the center of the right and left sides of the vest;
small upper pockets formed on at least one side of the right and left sides of the top front of the vest, at least some of said upper pockets having narrow elongate configuration for retaining elongate objects for ready access, and a pen and flash light contained in the small upper pockets of narrow elongate configuration;
loop holding means formed on at least one side of the right and left sides of the top front of the vest and airway means contained in said loop holding means;
and a first extra-large pocket formed across the outside back of the vest comprising an extra-large pocket cover panel secured along the top and bottom across the back of the vest, said extra-large pocket being openable on the sides and formed with quick release closure means along the sides and tabs for pulling open the sides, and a large multi-trauma dressing pad contained in the extra-large pocket formed across the outside back of the vest.

17. The EMS system of claim 16 further comprising a plurality of inside pockets including third and forth large pockets across the bottom inside right and left sides of the vest and a second extra-large pocket across the inside back of the vest, said inside pockets being formed with quick release closure means along the top of each inside pocket, said vest further comprising an intravenous fluid container and intravenous administration set contained in pockets of the vest.

18. The EMS system of claim 16 comprising a breathing tube and filter foam block coupled to one end of the breathing tube, said breathing tube and filter foam block being secured to the inside of the vest and arranged with the free end of the breathing tube adjacent to an opening of the vest for access for breathing through the filter foam block by EMS personnel wearing the vest.

19. The EMS system of claim 16 further comprising a safety harness, said safety harness comprising a belt formed around the waist of the vest and secured to at least a portion of the inside of the vest so that the pockets may be accessed and the vest opened while supporting EMS personnel wearing the vest with the safety harness.

20. An emergency medical response (EMS) system for delivering primary care emergency treatment and EMS equipment and supplies by EMS personnel comprising:

a personnel vest constructed and organized for carrying EMS equipment and supplies in a wearable and accessible arrangement, said vest being formed with a neck, two armholes and a waist opening, and an overlapping placket at the center front of the vest extending between the neck and waist openings, said placket being formed with quick release closure means for rapidly opening the vest;

quick release support loops at the shoulders of the vest for securing the ends of a stethoscope and for carrying a stethoscope around the back of the neck and on the shoulders of EMS personnel wearing the vest;

said vest comprising a plurality of outside pockets arranged on the front left and right sides of the vest with first and second large outside pockets across the front bottom left and right sides respectively of the vest for carrying bulkier EMS equipment and supplies at lower center of gravity and a plurality of intermediate size pockets across the center left and right sides of the front of the vest for carrying intermediate and smaller size EMS equipment and supplies;

small upper pockets formed on at least one side of the right and left sides of the front top of the vest at least one of said upper pockets having narrow elongate configuration for retaining elongate objects for ready access;

loop holding means formed on at least one side of the top front of the vest for holding airway means;

and a first extra-large pocket formed across the outside back of the vest comprising an extra-large pocket cover panel secured along the top and bottom across the back of the vest, said extra-large pocket being openable and accessible on the sides and formed with quick release closure means along the sides and with tabs for pulling open the sides for storing and accessing a large multi-trauma dressing pad.

* * * * *